(12) United States Patent
Vieira et al.

(10) Patent No.: US 9,207,185 B2
(45) Date of Patent: Dec. 8, 2015

(54) AUTOMATIC CLASSIFICATION OF THE DEGREE OF MATURATION FOR IRON ORE PELLETS

(71) Applicants: VALE S.A., Rio de Janeiro (BR); FACULDADES CATÓLICAS, Rio de Janeiro (BR)

(72) Inventors: Maria Beatriz Vieira, Nova Lima (BR); Sidnei Paciornik, Rio de Janeiro (BR); Otavio da Fonseca Martins Gomes, Rio de Janeiro (BR); Karen Soares Augusto, Rio de Janeiro (BR); Aloísio Antônio Melo Borges, Belo Horizonte (BR)

(73) Assignees: VALE S.A., Rio de Janeiro (BR); FACULDADES CATOLICAS, Rio de Janeiro (BR)

( * ) Notice: Subject to any disclaimer, the term of this patent is extended or adjusted under 35 U.S.C. 154(b) by 78 days.

(21) Appl. No.: 14/038,221

(22) Filed: Sep. 26, 2013

(65) Prior Publication Data
US 2014/0093136 A1    Apr. 3, 2014

Related U.S. Application Data

(60) Provisional application No. 61/707,717, filed on Sep. 28, 2012.

(51) Int. Cl.
| G01N 21/84 | (2006.01) |
| G06K 9/62 | (2006.01) |
| G06K 7/00 | (2006.01) |
| G06T 7/00 | (2006.01) |

(52) U.S. Cl.
CPC .............. G01N 21/84 (2013.01); G06K 9/6267 (2013.01); G06T 7/0004 (2013.01); G06T 2207/10056 (2013.01); G06T 2207/20036 (2013.01); G06T 2207/30136 (2013.01)

(58) Field of Classification Search
CPC ...................... B22F 2998/10; B22F 2003/166
See application file for complete search history.

(56) References Cited

U.S. PATENT DOCUMENTS

2010/0237280 A1* 9/2010 Barnes et al. ............ 252/182.33
2013/0027540 A1* 1/2013 Ito ................................. 348/79

* cited by examiner

*Primary Examiner* — Amir Alavi
*Assistant Examiner* — Kenny Cese
(74) *Attorney, Agent, or Firm* — Arent Fox LLP

(57) ABSTRACT

An automatic method or the classification of the Degrees of Maturation (DM) for fired iron ore pellets, independent of human intervention, based on the digital acquisition of microscopy images of polished cross sections, and their processing, analysis and classification by a suitable software procedure.

16 Claims, 4 Drawing Sheets

AUTOMATIC CLASSIFICATION OF THE DEGREE OF MATURATION FOR IRON ORE PELLETS

This application claims priority from U.S. Patent Application No. 61/707,717, titled "Automatic Classification of the Degree of Maturation of Iron Ore Pellets", filed on Sep. 28, 2012, and which is incorporated herein by reference in its entirety.

FIELD OF THE INVENTION

Aspects of the present invention refer to an automatic method for the classification of the Degrees of Maturation (DM) of fired iron ore pellets, independent of human intervention. An example method is based on the digital acquisition of microscopy images of polished cross sections, and their processing, analysis and classification by a suitable software procedure.

BACKGROUND OF THE INVENTION

Iron ore pellets are spherical agglomerates of iron ore super-fines (below 0.25 mm). Pellets undergo thermal processing to increase their compressive strength, which is important during handling and shipping, and during their use in reduction reactors. During thermal treatment several physico-chemical reactions occur, leading to strong changes in microstructure. These changes can be described by "degrees of maturation" (DM), and can be classified in classes in order to represent the microstructural characteristics. Typically DM is divided into four levels: A, B, C, and D, although intermediate types, such as AB, BC, and CD can also be obtained. The Degrees of Maturation increase from A to D, considering class A as the lowest Degree of Maturation and class D as the highest Degree of Maturation.

Usually, the DM is defined by observation of a cross section of the sample under the optical microscope. A trained human operator observes the images, either directly on the microscope eyepiece, or on a digital display, and decides the DM for that field of view. This decision is based on several parameters such as particle shape, porosity, presence of ferrite and slag formation. This represents a complex classification problem that has a strong subjective component, leading to errors and lack of reproducibility. FIGS. 1 to 4 show typical images for classes A, B, C, and D.

SUMMARY OF THE INVENTION

This invention aims to overcome this scenario, characterized by the human intervention that has a strong subjective component, leading to errors and lack of reproducibility, by an automatic method for the classification of the DM of fired iron ore pellets independent of human intervention.

DESCRIPTION OF PREFERRED EMBODIMENTS

The automatic method for the classification of the DM of fired iron ore pellets independent of human intervention is based on the digital acquisition of microscopy images of polished cross sections, and their processing, analysis and classification by a suitable software procedure, as described herein.

Referring to FIGS. 1-6, the image processing involves the steps of background correction, edge enhancement, segmentation, and morphological post-processing.

The image analysis provides several measurement parameters as listed below:

1. Field parameters: particle and pore count, particle and pore area fraction, particle mean lineal intercept.
2. Size parameters: particle and pore area, perimeter, calipers, equivalent circular diameter,
3. Texture parameters: field mean intensity of pixel intensities in a field image, standard deviation of pixel intensities in a field image, and Haralick parameters (that are statistical measurements of co-occurrence of neighboring grayscale pixels) measured from the pixel intensities in a field image.
4. Shape parameters: particle aspect ratio, convexity based on convex area and perimeter, circular shape factors based on area, perimeter and maximum caliper, branching and modification ratios based on inscribed circle diameter and minimum or maximum calipers.

This set of parameters was measured for hundreds of image fields representative of the 4 degrees of maturation (A, B, C, and D), and used as inputs to a supervised classification procedure. After cross-validation of more than 10,000 subdivisions of the measurement set, comparing the current method (human analysis) and the automatic method (software analysis), the global classification rate for the 4 classes reached 91.21%.

The classification of the images comprises 4 classes of Degrees of Maturation: A, B, C, and D and the Degrees of Maturation increases from A to D, considering class A as the lowest Degree of Maturation and class D as the highest Degree of Maturation.

Figure 1:
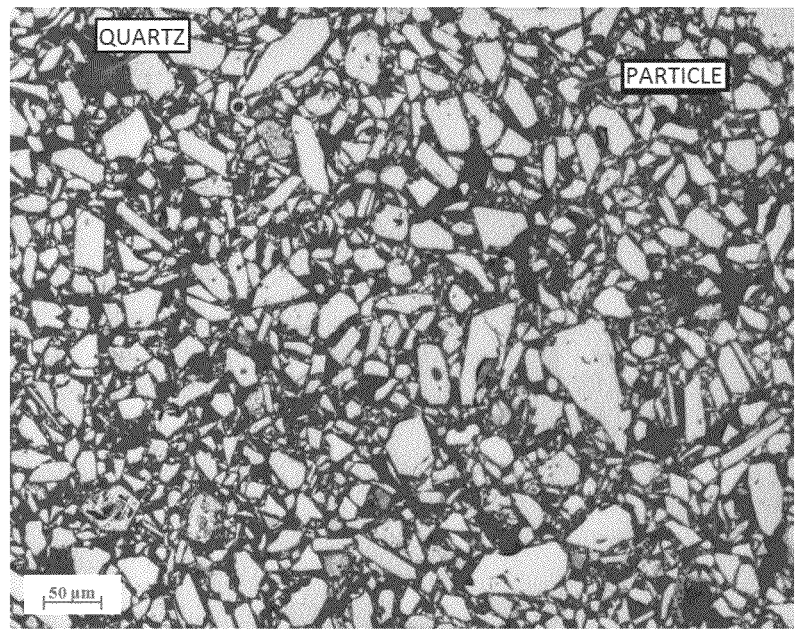
FIG. 1 shows an image for class A of DM.
Figure 2:
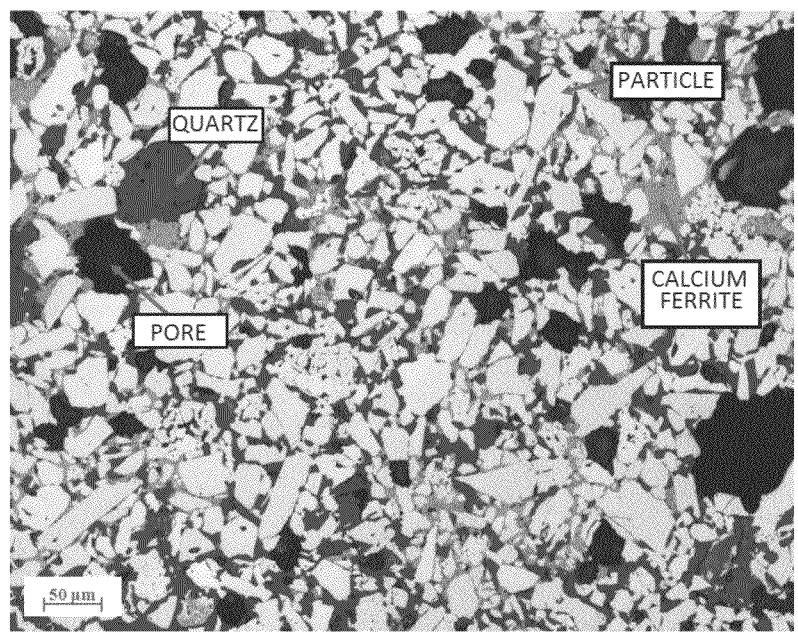
FIG. 2 shows an image for class B of DM.
Figure 3:
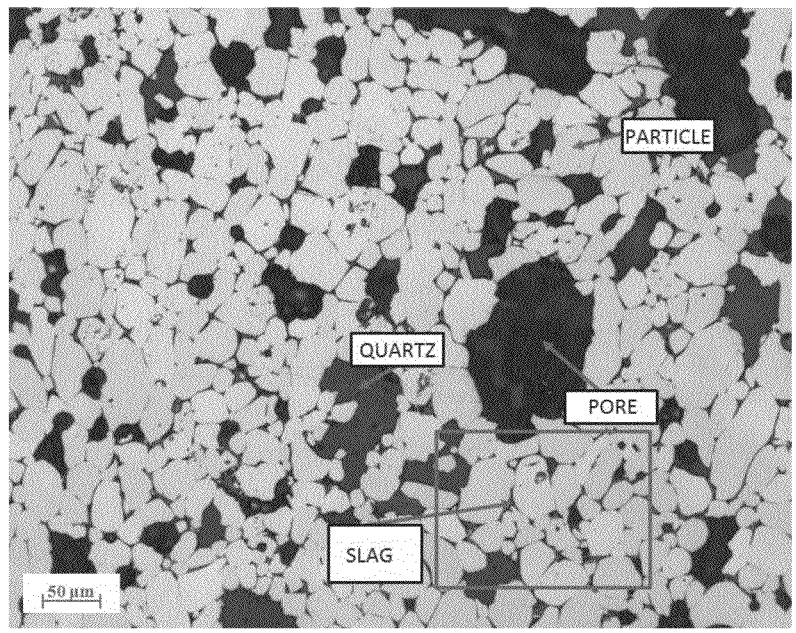
FIG. 3 shows an image for class C of DM.
Figure 4:
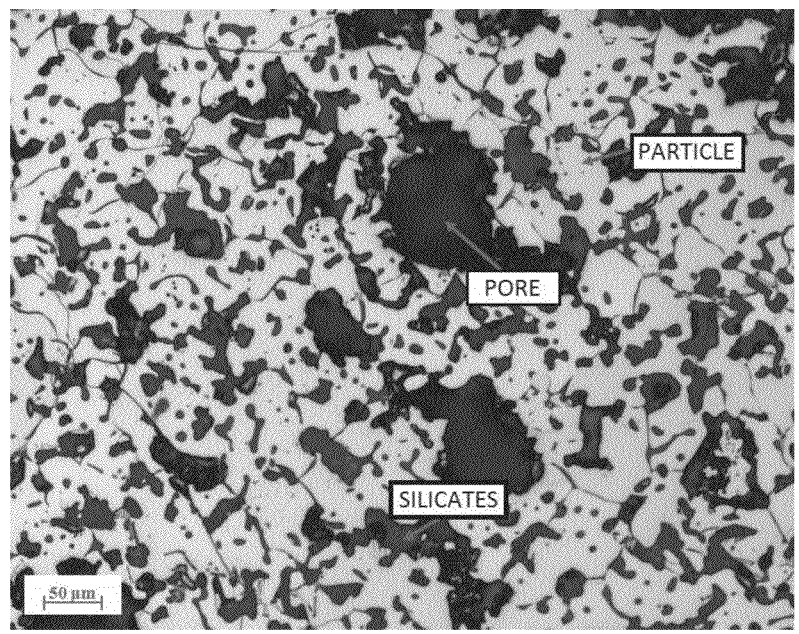
FIG. 4 shows an image for class D of DM.
Figure 5:
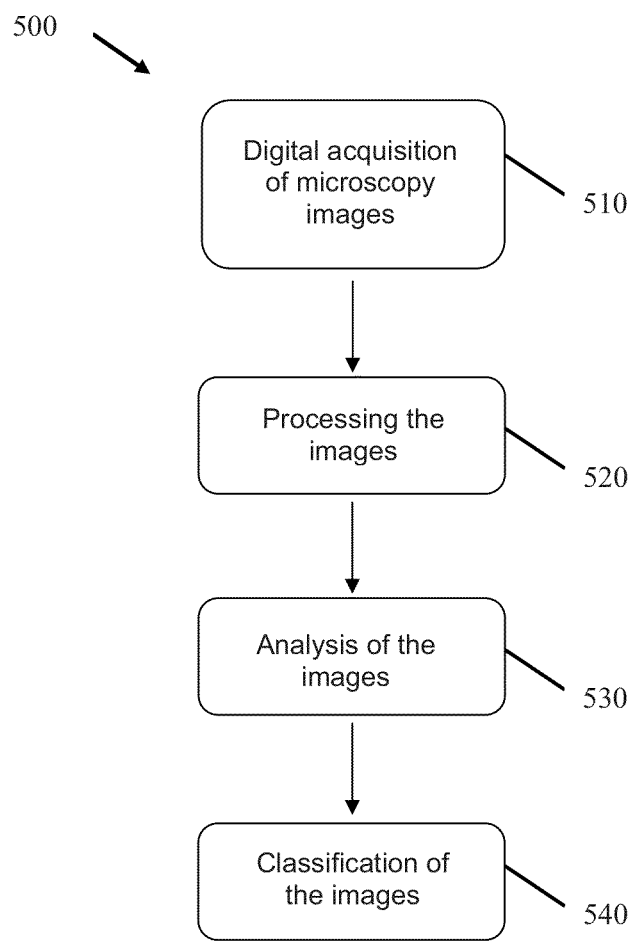
FIG. 5 is a flowchart of the automatic method provided by the present invention.
Figure 6:
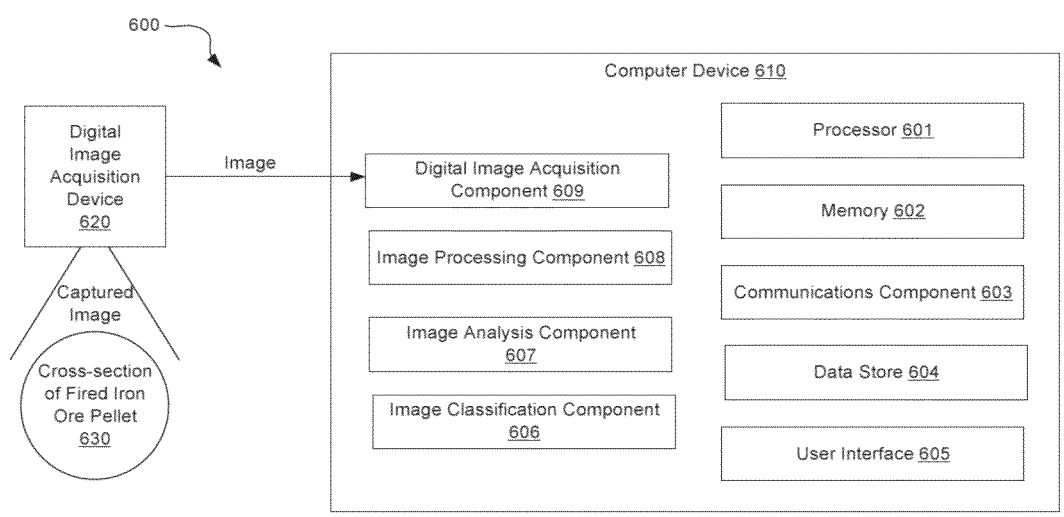
FIG. 6 is a system, including a computer device having components configured to perform aspects of the automatic method provided by the present invention.

In particular, referring to FIGS. 5 and 6, a system 600 may be configured to perform aspects of the automatic method 500 for the classification of the DM of fired iron ore pellets independent of human intervention.

The system 600 includes digital image capture device 620, such as, for example, a digital camera, which captures an image. The system 600 also includes a computer device 610, which, at 510 of method 500, acquires the captured image e.g., via a digital image acquisition component 609 from the digital image capture device 620. The image includes a first set of image data of a cross-section of a sample of a fired iron ore pellet 630. Although the digital image capture device 620 and the digital image acquisition component 609 are shown as separate components, they can be part of the same component. For example, digital image capture device 620 can be part of a computer device, such as the example of computer device 610, that also includes some or all of the other components shown in the example of computer device 610. In another example, some or all of the components shown in the example of computer device 610 may be included as part of digital image capture device 620.

Then, the computer device 610, at 520 of method 500, processes the image, e.g., via an image processing component 608, which may be software and/or hardware executing one or more of a background correction algorithm or function, an edge enhancement algorithm or function, a segmentation algorithm or function, and/or a morphological post-processing algorithm or function, to generate a revised image and/or a second or processed set of image data.

Next, the computer device 610, at 530 of method 500, analyzes the revised image and/or a second or processed set of image data, e.g., via an image analysis component 607, which may be software and/or hardware executing one or more algorithm or function to generate one or more image measurement parameters (e.g., field parameters, size parameters, texture parameters, and/or shape parameters) for the image.

Then, the computer device 610, at 540 of method 500, classifies the image, e.g., via an image classification component 606, which may be software and/or hardware executing one or more of an image classification algorithm or function by comparing the one or more image measurement parameters for the image to a set of one or more corresponding image classification parameter rules, e.g., which may include values or ranges for one or more representative image measurement parameters corresponding to each of one or more DM classifications. For instance, the image classification parameter rules may be based on samples from a supervised classification procedure used to quantify each class of DM. Based on achieving a certain degree of matching of values or ranges for one or more representative image measurement parameters, or otherwise meeting the image classification parameter rules for a certain DM class, the system thereby generates an association between the DM class and the image.

As such, each image and hence each sample of a fired iron ore pellet may be automatically evaluated and provided with a DM classification.

The computer device 610 also may include a processor 601 for carrying out processing functions associated with one or more of the components and functions described herein. The processor 601 can include a single or multiple set of processors or multi-core processors. Moreover, the processor 601 can be implemented as an integrated processing system and/or a distributed processing system.

The computer device 610 also may include a memory 602, such as for storing data used herein and/or local versions of applications being executed by processor 601. The memory 602 can include any type of memory usable by a computer, such as random access memory (RAM), read only memory (ROM), tapes, magnetic discs, optical discs, volatile memory, non-volatile memory, and any combination thereof.

The computer device 610 also may include a communications component 603 that provides for establishing and maintaining communications with one or more entities utilizing hardware, software, and services as described herein. The communications component 603 may carry communications between components within the computer device, as well as between the computer device and external devices, such as devices located across a communications network and/or devices serially or locally connected to the computer device. For example, the communications component 603 may include one or more buses, and may further include transmit chain components and receive chain components associated with one or more transmitters and receivers, respectively, or one or more transceivers, operable for interfacing with external devices.

The computer device 610 also may include a data store 604, which can be any suitable combination of hardware and/or software, that provides for mass storage of information, databases, and programs employed in connection with aspects described herein. For example, the data store 604 may be a data repository for applications not currently being executed by the processor 601.

The computer device 610 also may include a user interface component 605 operable to receive inputs from a user of the computer device 610, and further operable to generate outputs for presentation to the user. The user interface component 605 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, the user interface component 605 may include one or more output devices, including but not limited to a display, a speaker, a haptic feedback mechanism, a printer, any other mechanism capable of presenting an output to a user, or any combination thereof.

The main differences between the current method and the proposed Invention are summarized in the Table below:

TABLE 1

Main differences between the Current Method and the Automatic Classification

| Current Method | Automatic Classification |
| --- | --- |
| Human operator decides the degree of maturation | Automatic system determines the degree of maturation |
| Subjective and non-reproducible method | Objective and reproducible method |
| Strongly operator dependent | Independent of operator |
| Manual microscopy system | Automated microscopy system |

The examples set forth in the present application are for illustrative purposes only and are not intended to limit, in any way, the scope of the present invention.

As used in this application, the terms "component," "module," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or actions described above.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of codes and/or instructions on a machine readable medium and/or computer readable medium, which may be incorporated into a computer program product.

In one or more aspects, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

The invention claimed is:

1. An automatic method for classification of a Degree of Maturation (DM) for a fired iron ore pellet, comprising:
    digital acquisition of a microscopy image of a polished cross section of the fired iron ore pellet;
    processing the image to generate a revised image;
    analyzing the revised image to generate one or more image measurement parameters; and
    classifying the image via an image classification component, including executing one or more image classification functions for:
        comparing the one or more image measurement parameters for the revised image to a set of one or more corresponding image classification parameter rules corresponding to each of one or more DM classifications, wherein each of the one or more DM classifications represents a change in a microstructural characteristic of the fired iron ore pellet during thermal treatment; and
        assigning the image a DM classification from the one or more DM classifications based on the one or more image measurement parameters for the revised image meeting the set of one or more corresponding image classification parameter rules corresponding to the DM classification.

2. The method of claim 1, wherein the processing of the image includes one or more of background correction, edge enhancement, segmentation, and morphological post-processing.

3. The method of claim 1, wherein the analyzing of the image comprises generating one or more types of measurement parameters selected from the group consisting of field parameters, size parameters, texture parameters, and shape parameters.

4. The method of claim 3, wherein the field parameters comprise particle and pore count, particle and pore area fraction, and particle mean lineal intercept.

5. The method of claim 3, wherein the size parameters comprise particle and pore area, perimeter, calipers, and equivalent circular diameter.

6. The method of claim 3, wherein the texture parameters comprise a mean intensity of pixel intensities in a field image, a standard deviation of pixel intensities in a field image, and Haralick parameters measured from the pixel intensities in the field image.

7. The method of claim 3, wherein the shape parameters comprise particle aspect ratio, convexity based on convex area and perimeter, circular shape factors based on area, perimeter and maximum caliper, branching and modification ratios based on inscribed circle diameter and minimum or maximum calipers.

8. The method of claim 1, wherein the DM is represented by a class selected from the group consisting of A, B, C, and D and intermediate types AB, BC, and CD.

9. The method of claim 8, wherein the DM increases from A to D.

10. The method of claim 1,
    wherein the digital acquisition of the microscopy image is via a digital image capture device or a digital image acquisition component;
    wherein the processing of the image is via an image processing component; and
    wherein the analyzing of the image is via an image analysis component.

11. The method of claim 1, wherein the method is reproducible.

12. The method of claim 1, wherein the method is independent of an operator.

13. The method of claim 1, wherein the method employs an automated microscopy system.

14. The method of claim 1, wherein the set of one or more corresponding image classification parameter rules include values or ranges for one or more representative image measurement parameters corresponding to each of the one or more DM classifications.

15. The method of claim 1, wherein the measurement parameters comprise at least one of particle and pore count, particle and pore area fraction, particle mean lineal intercept, particle and pore area, perimeter, calipers, equivalent circular diameter, a mean intensity of pixel intensities in a field image, a standard deviation of pixel intensities in a field image, Haralick parameters measured from the pixel intensities in the field image, particle aspect ratio, convexity based on convex area and perimeter, circular shape factors based on area, perimeter and maximum caliper, or branching and modification ratios based on inscribed circle diameter or minimum or maximum calipers.

16. The method of claim 8, wherein the Degrees of Maturation increase from A to D, considering class A as the lowest Degree of Maturation and class D as the highest Degree of Maturation.

\* \* \* \* \*